United States Patent [19]
Mani et al.

[11] Patent Number: 5,814,498
[45] Date of Patent: Sep. 29, 1998

[54] PROCESS FOR THE RECOVERY OF ORGANIC ACIDS AND AMMONIA FROM THEIR SALTS

[75] Inventors: K. N. Mani, Decatur; D. Kent Hadden, Mt. Zion, both of Ill.

[73] Assignee: Archer Daniels Midland Company, Decatur, Ill.

[21] Appl. No.: 639,831

[22] Filed: Apr. 29, 1996

[51] Int. Cl.$^6$ .................. C12P 7/40; C12P 7/56; B01D 61/00; B01D 15/04
[52] U.S. Cl. .................. 435/136; 204/527; 204/530; 204/534; 204/536; 204/537; 204/538; 210/259; 210/630; 210/637; 210/638; 210/641; 210/651; 435/137; 435/140; 435/144; 435/800
[58] Field of Search ................. 210/637, 654, 210/259, 630, 638, 641, 651; 435/136, 139, 137, 140, 144, 800; 204/527, 530, 534, 536, 538, 537, 540

[56] References Cited

U.S. PATENT DOCUMENTS 5,681,728  10/1997  Miao et al. ................. 435/136

FOREIGN PATENT DOCUMENTS

WO 96/41012  6/1995  WIPO.

*Primary Examiner*—Herbert J. Lilling
*Attorney, Agent, or Firm*—Laff, Whitesel, Conte & Saret, Ltd.

[57] ABSTRACT

A process recovers organic acid and ammonia from their salts preferably obtained from microbial fermentation of a saccharide in a nutrient. The fermented materials is passed through a nanofiltration or a chelating resin ion-exchange bed or a combination of both a nanofilter and a chelating resin ion-exchange bed in order to reduce divalent or multivalent metal contaminants. Then, the filtered material is processed in a multi compartment electrodialysis containing bipolar and anion membranes.

11 Claims, 8 Drawing Sheets

PROCESS FOR THE RECOVERY OF ORGANIC ACIDS AND AMMONIA FROM THEIR SALTS

FIELD OF THE INVENTION

This invention relates to processes for recovering a variety of organic acids from their ammonium salts, and more particularly to monobasic acids such as lactic acid and acetic acid as well as to certain low molecular weight dibasic acids such as fumaric, succinic, malic, maleic and other acids.

The acids may be obtained from a fermentation conversion of saccharides (substrates) such as starch, sucrose or glucose or from n-paraffins. The microbes used in the fermentation process may be Protists (yeast or fungi) or bacteria. The fermentation itself may be either aerobic or anaerobic. For producing certain organic acids, enzymes may be used in place of microbes. The pH in the fermenter is maintained in the range of about 3 to 9 through an addition of ammonia (base). The improvement disclosed in this invention is of particular value in a continuous fermentation processes.

In order to achieve a continuous operation of the fermentation process, the organic acid product has to be removed from the fermenter at a rate equal to its production, while retaining within the fermenter the microbe nutrients and any unconverted substrate. Alternatively, a continuous recovery process for returning these materials to the fermenter has to be in place. An additional enhancement is to recover the base component for reuse in the fermenter for pH adjustment. In this context, bases which have large solubility in water, e.g. ammonia, sodium hydroxide and potassium hydroxide would be preferred over lime, because they are easy to recover and reuse.

U.S. Pat. No. 4,882,277 describes a continuous fermentation process that uses electrodialysis for removing the organic acid from the fermentation mixture. A four compartment cell containing one cation membrane, two anion membranes and a set of electrodes is used to effect the recovery. Preferably, after a microfiltration step (to remove the microbial cells), the fermentation broth containing the product acid in its salt form is circulated through a basification loop of the electrodialysis cell. A direct current driving force splits the organic acid, which is present in its salt form, into the component acid and base. The base is retained with the fermenter broth and is returned to the fermenter along with any recovered microbial cells.

Alternatively, U.S. Pat. No. 4,882,277 teaches an electrodialysis cell containing a cation exchange membrane, an anion exchange membrane, a set of bipolar membranes and anion membranes, an anion membrane and a set of electrodes which achieve the same end result. A problem with this process is that the microfiltration step (considered optional) does not remove any of the dissolved high molecular weight byproducts such as proteins or certain soluble nutrients which are present in the fermenter broth, which results in membrane fouling that forces a process shutdown after only a limited run time. Additionally, and in particular, when non-volatile bases such as NaOH and KOH are used, the precipitation of divalent metal impurities on the surfaces or inside the membranes would result in a high power consumption and an unstable long term operation.

U.S. Pat. No. 5,002,881 describes the production of lactic acid via a culture bacilli of the genus *Bacillus,* followed by ultrafiltration and reverse osmosis that concentrates the permeate. Subsequently, the resulting outflow is subjected to an electrodialysis wherein bipolar membranes are used to decompose the lactate into lactic acid and base (XOH; where X and $NH_4$ or a metal having a hydroxide and a salt of lactic acid which are water soluble).

This U.S. Pat. No. 5,002,881 patent and an earlier article (K. N. Mani, Electrodialysis water splitting Technology, *J. Membrane Sci.,* 58 (1991) pp 117–138) use a three-compartment electrodialysis cell comprising bipolar, cation and anion membranes; wherein, the feed salt is introduced into the compartment between the cation and anion membranes. This process version has some of the same shortcomings that are found in the earlier processes, since the ultrafilter is not significantly more effective than the microfilter in removing the membrane foulants. Furthermore the use of reverse osmosis and three compartment electrodialysis processing increases both the process complexity and the cost. When producing bases such as NaOH and KOH, the cation membrane in the electrodialysis cell is easily fouled by divalent metal impurities ($Ca^{+2}$, $Mg^{+2}$) which are part of the fermenter nutrients and which are present in the feed salt. With $NH_4OH$ as the base, the divalent metals do have a higher solubility and most likely will not foul the membrane at the modest concentration levels found in the fermenter. However, the resulting poor electrical conductivity of the base would lead to higher power consumption.

U.S. Pat. No. 4,882,247 describes a process for producing, recovering and purifying lactate from a fermentation broth and its subsequent conversion to lactic acid via membrane electrodialysis by using Lactobacillus acidophilus IAM 3532. In this process, the broth is at a pH of 5–5.7 and contains 75–90 gm/l of lactate acid which is subjected to electrodialysis in a cell containing cation and anion membranes to produce a high concentration of lactate salt that is free of microbial cells and most other impurities. To obtain the acid and base, the cells are recycled to the fermenter, while the concentrated lactate sale is processed in a secondary electrodialysis cell containing bipolar and cation membranes. In effect, this process uses two stages of electrodialysis. The fouling/pluggage of the first electrodialysis cell by microbial cells and the fouling of the cation membranes in the secondary cell by the divalent impurities are problems that add further complexity to the process.

Canadian Patent 2,133,168 claims a fermentative process for lactic acid and glycerol. The process uses strains of rod-like cells of Lactobacillus to convert free sugars in order to obtain >5 gm/100 ml of lactate at a pH of 4.5–5.5. The lactate, cells, and water are separated by a multistep process involving ultrafiltration (0.1–0.375µ pores) to recover suspended solids and "heavies" which are present in the broth. Following the ultrafiltration, there is a nanofiltration (150 Daltons rating) of the permeate to separate the higher molecular weight impurities. Subsequently, a reverse osmosis step (50 Daltons rating) removes the excess water to concentrate the dilute lactic salt and glycerol. The process separates the various sizes of organic molecules and water, but it does not separate the acid and alkali (base) from the salt.

J. S. Han and M. Cheryan (*J. Membrane Sci.* 107, (1995)) have studied the nanofiltration of model acetate solutions such as might result from fermentation. The cited goal is to recycle components, such as glucose and cells, in quantities that reduce the cost of the fermentation. Neither processing the feed stream to obtain the product organic acid nor the impact of contaminants in the conversion operation is addressed.

SUMMARY OF INVENTION

Accordingly, an object of this invention is to provide both new and improved continuous fermentation process for removing organic acid and ammonia from their salts. In this connection, an object is to provide a system for carrying on such a process which does not foul membranes used in the process. Here, an object is to recover microbes, nutrients, and unconverted substrate from a feed stream central to the continuous process.

In keeping with an aspect of this invention, these and other objects are accomplished by a process for continuously recovering organic acids and ammonia from their salts. These salts may first be obtained by a microbial fermentation of a saccharide in the presence of the requisite nutrients. The pH in the fermenter is maintained in the range of about 3–9 through a use of ammonia or an ammonium hydroxide solution, most of which is recycled from a downstream recovery step. The process yields a dilute organic salt solution. The specific process steps are:

Recovering from a fermenter a stream substantially free of microbial cells through the use of a coarse or micro filter;

Subjecting the recovered solution to a suitable means for removing divalent and multivalent metals, the means preferably being a nanofiltration (~200 Dalton rating) in order to remove dissolved higher molecular weight organics as well as to reduce the amount of divalent metal ions to a level below 15 ppm. In the alternative, a chelating resin cation exchange bed may be used in place of or in tandem with the nanofilter in order to achieve an adequate reduction in the level of the divalent metal contaminants;

Processing the resulting organic salt solution in either a two compartment electrodialysis cell or a stack of electrodialysis cells containing bipolar and anion membranes in order to generate a concentrated organic acid product solution and an alkaline solution that is substantially depleted in its organic salt content; and Combining the alkaline solution with the retentate from the nanofiltration step, sterilizing it as may be appropriate, and recycling it back to the fermenter.

The concentrated acid stream from the electrodialysis step contains up to 10% of its organic content in the form of its ammonium salt and is processed further to recover pure acid.

BRIEF DESCRIPTION OF THE DRAWINGS

A preferred embodiment will become more apparent from the following description, taken with the accompanying drawings in which.

DETAILED DESCRIPTION OF THE PROCESS

Figure 1:
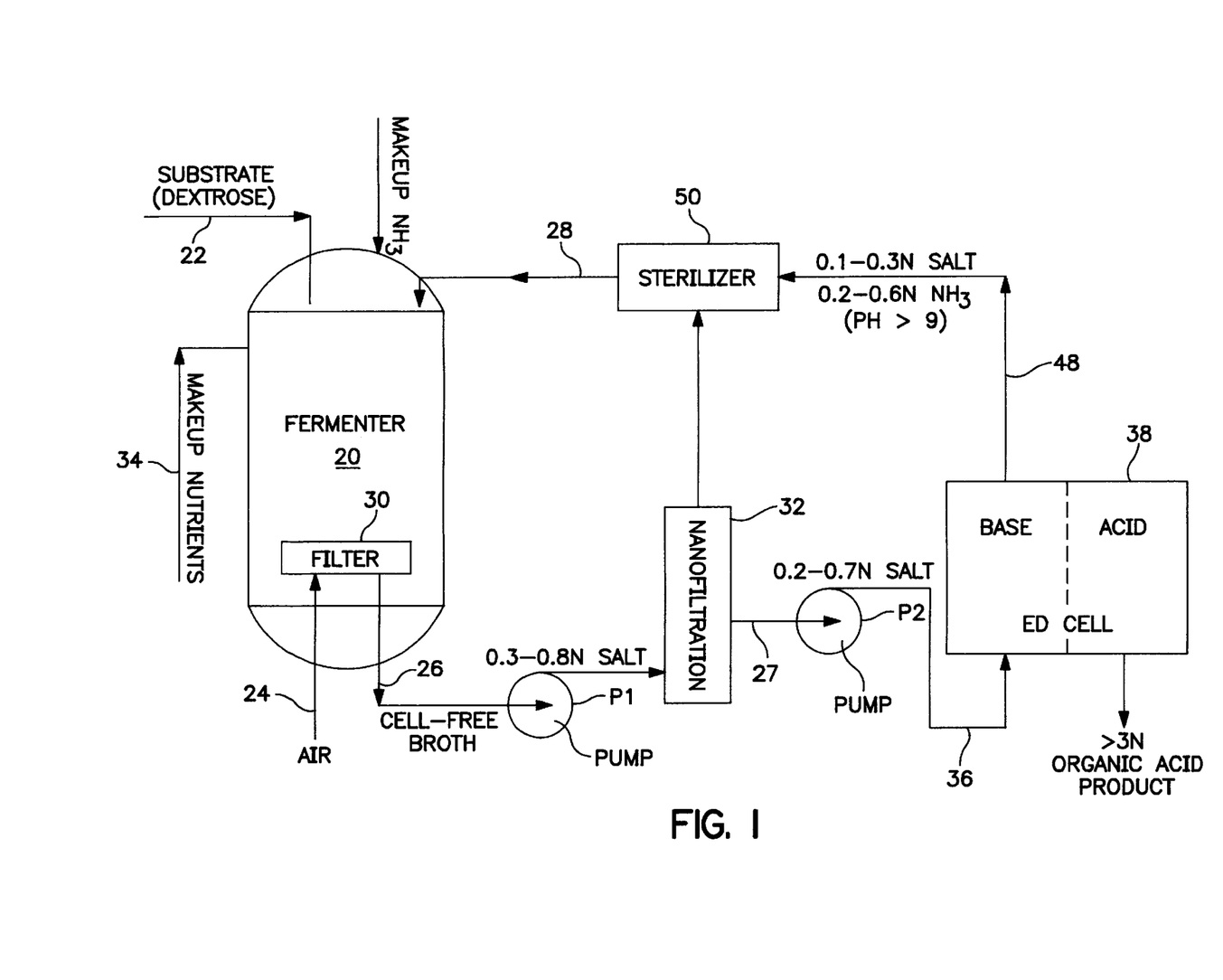
FIG. 1 is a flow chart schematically showing the equipment for a continuous fermentation process using nanofiltration.
Figure 1A:
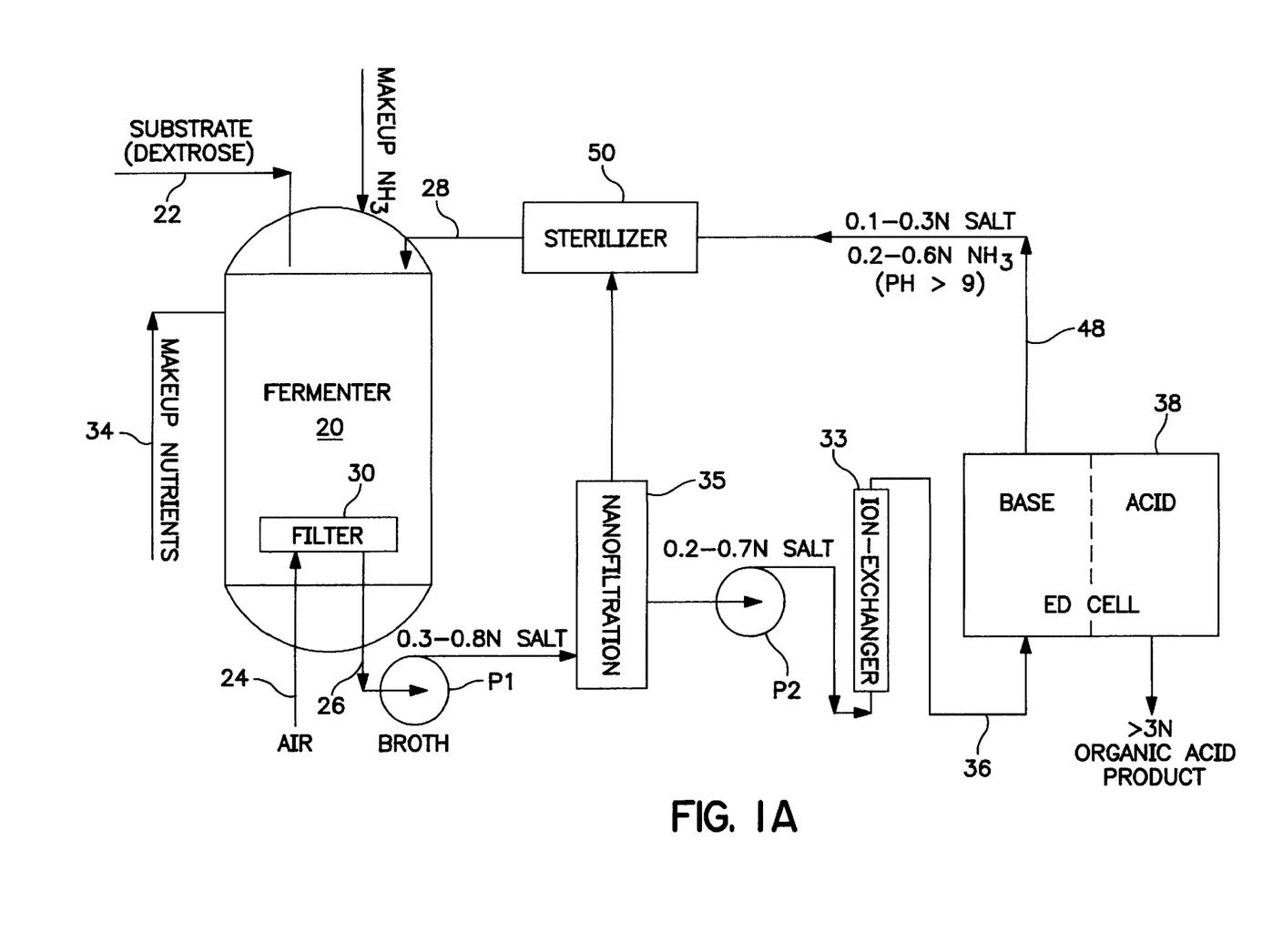
FIG. 1A shows a similar flow chart of a process using an ion-exchanger.

Two examples of systems incorporating the improved recovery process of this invention are shown schematically in the attached FIG. 1 and FIG. 1A. The difference between these two systems is that the system of FIG. 1 uses a nanofilter while FIG. 1A uses a chelating resin ion-exchanger.

The fermenter 20 performs a fermentation step on a substrate in order to obtain the organic acid in any suitable and known manner. The process starts with an introduction of an initial load of the substrate, as indicated at 22. The initial load introduced into the fermenter includes a microorganism, dilution water and a set of nutrients such as: potassium phosphate, calcium carbonate, magnesium sulfate and other trace materials. Ammonia is metered into the fermenter as needed in order to maintain the pH within the target range of 3 to 9. For aerobic fermentation, air is sparged in at a set rate via pipe 24. As the organic salt/acid concentration builds up above the target level of ~0.3N, it is withdrawn at outlet 26 and processed further to recover a portion of the organic acid. The balance of the concentration and the recovered ammonia is recycled back to the fermenter 20 via pipe 28.

The lines 26 and 27 include any suitable pumps P1, P2 for transferring the fluids. The nature (0.3–0.8N and 0.2–0.7N) of the fluids being transferred is shown in FIGS. 1 and 1A. The letter "N" indicates "normality" which is a dimensionless index found by dividing grams by the molecular weight of the fluid being transferred.

The first step in the recovery process is to obtain a pre-filtered fermenter output filtrate stream that is essentially free of the microbial cells. Since yeast and fungi have a relatively larger diameter and have a propensity to form large aggregates, this pre-filtration can be readily achieved through a use of "coarse" screens, which are located at 30, preferably within the fermenter body. The feed stream enters through one side of the coarse screen while the clearer filtrate exits on the other side. When the coarse screens are located at 30 inside the fermenter, the screens are kept free of blockage through a use of the air sparge from pipe 24; or in the case of anaerobic fermentation by a use of a $CO_2$ gas sparge (for example) or by a recycle liquid back flush. When the fermentation is carried out with bacteria, the separation is achieved through a use of fine mesh filters (or microfilters). Alternatively, the pre-filter coarse screens could be located in an external loop (not shown) such as in pipe 26, for example. One advantage of locating the filtration unit in a loop external to the fermenter is the ease of removal and replenishment of the microbes. However, the internal screen is simpler and works well with the larger fungi.

The pre-filtrate from filter 30 is substantially free of the microbial cells and is then subjected to nanofiltration at 32 to remove the dissolved higher molecular weight impurities and, importantly, to reduce the amount of divalent metals content to a level below 15 ppm total. Principally, the divalent metals comprise calcium and magnesium, but may also include other metals (such as barium, strontium and zinc) which form insoluble precipitates at pH's >9. The nanofiltration step at 32 (FIG. 1) recovers the ammonium salt of the acid along with any free organic acid while retaining any particulates from the pre-filtration step at 30, dissolved higher molecular weight organics and the divalent metals in the retentate loop for subsequent recycle back to the fermenter 20. The nanofilter at 32 usually recovers about 30–80% of the organic acid values present in the feed. This rate of recovered organic acid is 125–333% of the rate produced in the fermenter at steady state. The retentate from the nanofiltration step contains essentially all the nutrients, while its overall organic salt content is reduced.

The removal of the divalent metals from the organic salt may also be achieved through a use of a chelating resin ion-exchange bed 33 (FIG. 1A) used in conjunction with or in addition to the nanofilter 32 or another filter. It should be noted that many of the chelating resins are most effective in removing the divalent metals at pH's of 7 or higher. In this case, one may use a microfilter 35 upstream of the ion-exchanger in order to obtain a sufficiently clarified pre-filtrate as a feed stream to the ion-exchange unit. The spent resin is regenerated with acid and ammonia and make up nutrients are added to the fermenter at 34, as needed.

Figure 2:
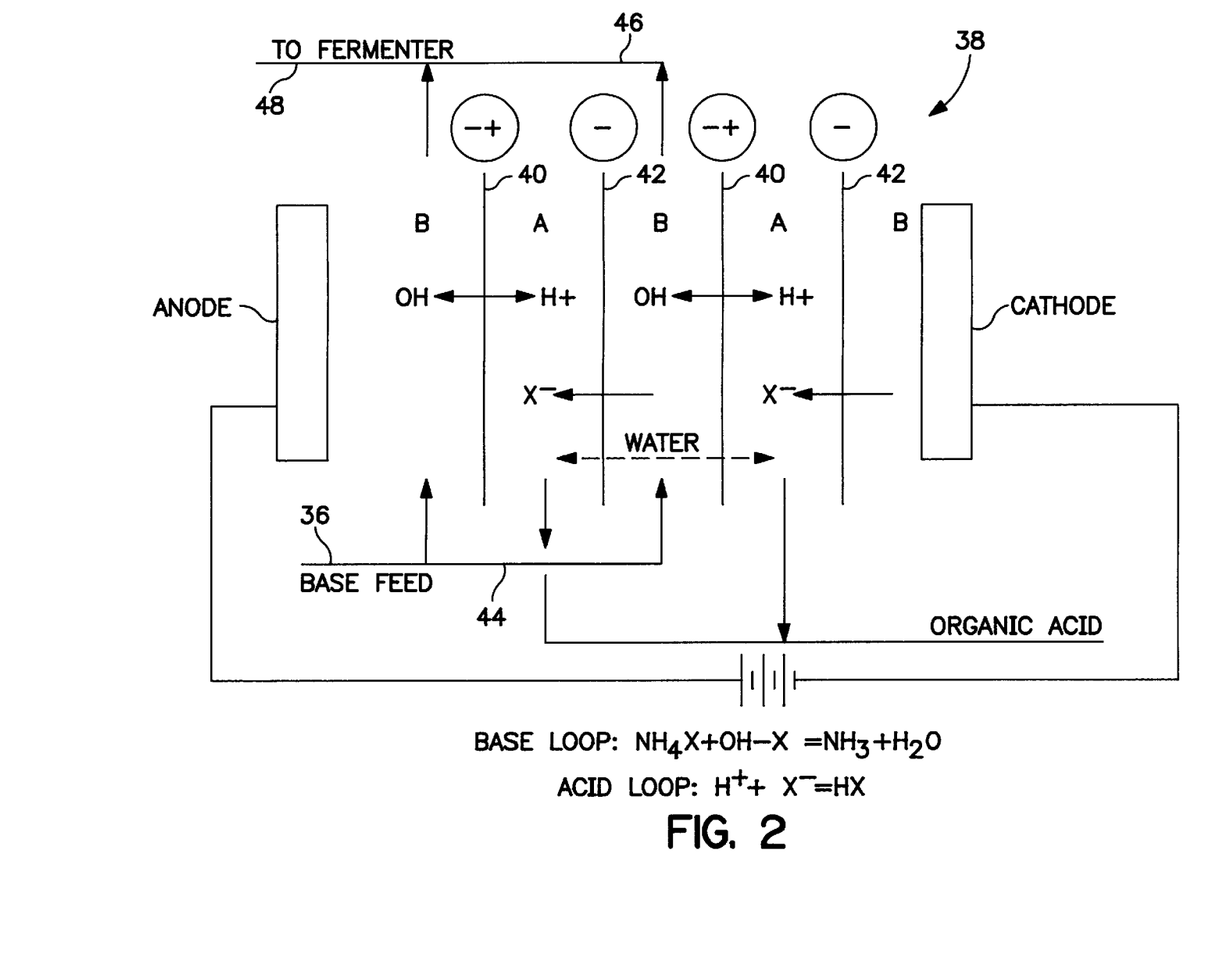
FIG. 2 is a schematic showing of a two-compartment anion electrodialysis cell.

The permeate from the nanofiltration 32 (or chelating resin ion-exchanger 33) is then fed at 36 to the electrodialysis (ED) cell unit 38 comprising bipolar and anion exchange membranes. FIG. 2 shows an ED cell unit that may be used for the unit 38 (FIG. 1). The cell comprises, in sequence, a base compartment (B), a bipolar membrane 40 (+–), an acid compartment (A), and an anion membrane 42 (–). As many as 100–250 such unit cell may be stacked or assembled into a single electrodialysis unit 38. The feed to the individual compartments within the unit is achieved through a set of internal manifolds 44, 46. The separation process is driven by a direct current applied across set of electrodes (e.g. an anode on the left and a cathode on the right) at the two ends of the ED unit 38. A unit such as that shown in FIG. 2 is called a two-compartment cell because only two compartments, A and B are separated by the two types of membranes 40, 42.

In FIG. 2, the filtrate from either the nanofiltration unit 32 (FIG. 1) or the chelating resin ion-exchanger 33 (FIG. 1A) is fed in via pipe 36 and manifold 44 to the B chambers. There, under the influence of the direct current, the organic anion $X^-$ resulting from the dissociation of the salt, $NH_4X$ is transported across the anion membranes 40 to the A chambers. Concurrently, $OH^-$ ions are generated at the anion layer of the bipolar membrane. These $OH^-$ ions combine with the $NH_4^+$ ions in the base compartment to form $NH_4OH$, which tends to exist as dissolved, undissociated ammonia, $NH_3$ ($NH_4OH \leftrightharpoons NH_3 + H_2O$). Consequently, its ionic transport across anion membranes is inhibited. Concurrently, $H^+$ ions are generated at the cation layer of the bipolar membrane in the A chambers. The combination of the $H^+$ ion with the $X^-$ ion in the A chambers results in the formation of the organic acid, HX.

There is some electro-osmotic transport of water from the B chamber to the A chambers as well as some ammonia (diffusive transport). In most instances therefore, there is no need to add makeup water to the acid loop. The product acid is withdrawn at a high concentration in the order of 3–4N. On an overall basis, the feed stream of organic salt, which is at a concentration of 0.2–0.7N, is converted to a basified (i.e., ammonia laden) solution that has been depleted of its salt content, while generating a concentrated acid product.

The basified solution from the ED unit 38 is then combined at 50 (FIG. 1) with the retentate from the nanofiltration unit, sterilized as required, and returned to the fermenter 20 via pipe 28. The overall process is able to selectively recover the acid values, while substantially all of the unconverted substrate, microbial cells and the nutrients as well as the base (ammonia) for pH adjustment are returned to the fermenter 20. Thus, the continuous operation of the fermenter is facilitated and enhanced.

We have found that the removal of divalent metals, particularly calcium and magnesium, has a surprisingly beneficial effect in terms of improving the efficiency of the downstream operation for recovering the acid and ammonia values from the organic salt stream. Heretofore, these metals have apparently formed an insoluble hydroxide film on the bipolar membranes. This film has significantly reduced the current throughput that is needed for the production of the organic acid and ammonia from the salt stream. This mechanism of divalent metal fouling is different from the fouling that is encountered with cation membranes in systems such as those used for chlor-alkali production wherein the divalent metals precipitate within the cation membrane, causing higher power consumption due to irreversible fouling.

The maximum level of these contaminants is determined by their solubility in the depleted basified organic salt solution in the base loop of the electrodialysis unit. Such solutions nominally contain 0.1–0.3N organic salt and have a pH in a range of 9 to 10.5. The combined concentrations of the divalent metal concentrations in such solutions, at room temperature, is ~15 parts per million (ppm) and somewhat lower at higher temperatures. For stable long term operation of the ED unit, at a high current density, the total level of calcium and magnesium should be under 10 ppm, preferable below 5 ppm.

The nanofiltration membrane 32 (FIG. 1) or chelating cation exchange resin 33 (FIG. 1) for feed at a higher pH, preferably 7, is able to effectively reduce the divalent metals content to a level that enables a satisfactory operation of the ED unit, while enabling the organic salt to be recovered in high yield. We have found that nanofiltration membranes with a molecular weight cutoff of 200 Daltons are able to adequately handle the process needs.

The invention can be better understood from the following examples. Product organic salt from a commercial scale fermenter, such as 20, was the feed stream used in carrying out the various experiments. The primary organic salt from the fermenter was lactate, but minor amounts of fumarate, acetate and succinate were also present. Dextrose at a 99.5% level was used as the substrate in the fermenter. The product output at a pH of 4–5.5 was pre-filtered to remove essentially all of the microbial cells. The pre-filtrate thus obtained was clear to slightly cloudy and was noticeably colored. At a 450 nm wavelength, a commonly found color index, was 0.125 units.

Comparative Example A: Ultrafiltration of the pre-filtrate.

In the fermenter 20, the pre-filtrate was filtered at 30 through a standard ultrafiltration module (AMT-100 from Advanced Membrane Technology; nominal rating: 100,000 Daltons). Approximately 30 gallons of the initial feed stream material was subjected to a four-fold increase in concentration, resulting in ~22.5 gallons of filtrate and 7.5 gallons of concentrate. The resulting filtrate and concentrate were then analyzed for color, organics, Ca, Mg and Na. The results of this analysis are shown in the following Table 1. It should be noted that in this and the following examples, the reported figures for organic acids, such as lactic and fumaric acids, represent their total content, expressed as the organic acid. For example at a pH 5, substantially all of the lactic acid would be present in the form of the ammonium lactate salt.

TABLE 1

|  | Dextrose gm/l | Lactic gm/l | Glycerol gm/l | Fumaric gm/l | Ethanol gm/l | Color @ 450 nm | Na ppm | Ca ppm | Mg ppm |
|---|---|---|---|---|---|---|---|---|---|
| Feed | 5.55 | 37.25 | 10.95 | 1.84 | 4.63 | 0.125 | 1848 | 11.9 | 12.6 |
| Permeate | 5.56 | 38.23 | 11.33 | 1.81 | 3.79 | 0.050 | 1826 | 10.4 | 10.5 |
| Concentrate | 9.02 | 48.37 | 12.92 | 2.93 | 3.74 | 0.334 | 2444 | 21.4 | 23.2 |

It can be seen from Table 1 that the concentration of the various components in the permeate (i.e. the filtrate stream) is essentially identical to that in the pre-filtrate feed stream. In itself, this is not surprising, since the ultrafilter, rated at 200,000 Daltons, is really designed to remove precipitates and the dissolved macromolecules. The limited amount of retention for the various components as well a reduction in the color index is due to the buildup of a gel layer on the membrane surface. The resulting filtrate had a significant yellow color.

Comparative Example B: Nanofiltration of the pre-filtrate.

The pre-filtrate taken from filter 30 was filtered through a nanofilter module (Model Desal 5-DK, made by Desalination Systems nominally rated at 200 Daltons) at a feed pressure of ~120 psig. Approximately 30 gallons of the feed was processed, resulting in 24 gallons of permeate (i.e. filtrate) and 6 gallons of concentrate, representing a five fold concentration increase for the impermeables. The results were as shown on the following Table 2.

TABLE 2

|  | Dextrose gm/l | Lactic gm/l | Glycerol gm/l | Fumaric gm/l | Ethanol gm/l | Color @ 450 nm | Na ppm | Ca ppm | Mg ppm |
|---|---|---|---|---|---|---|---|---|---|
| Feed | 3.71 | 39.47 | 12.48 | 2.37 | 5.77 | 0.12 | 685 | 46.3 | 23.1 |
| Permeate | 0.87 | 32.68 | 12.38 | 1.29 | 5.83 | 0.009 | 584 | 3.84 | 0.8 |
| Concentrate | 6.12 | 65.04 | 14.6 | 7.99 | 4.38 | 0.72 | 1317 | 202 | 98.2 |

As seen from Table 2, the nanofilter recovers the organic salts in preference to the dextrose substrate. Also, the nanofilter has a high rejection for the divalent metals. The specific figures can be computed to be as follows:

Recovery of low molecular weight organics in the permeate stream:
Lactic: 66%
Fumaric: 44%
Glycerol: 79%
Ethanol: 81%
Rejection of dextrose and the metals:
Dextrose: 81%
Sodium: 31%
Calcium: 93%
Magnesium: 97%

The high rejection of the membrane for dextrose and the divalent metals is especially beneficial because these materials can be directly recycled via pipe 48, sterilizer 50 and pipe 28 back into the fermenter for reuse. The recoveries of the organic salts is high enough to permit an operation of the fermenter at a higher productivity level.

The following examples illustrate the electrodialysis conversion of the organic salt stream from the filtration step into a concentrated acid product wherein the acids are present in substantially a free acid form and a dilute basified stream which is combined with the concentrate from the filtration step and returned to the fermenter. The organic acid stream can then be purified and concentrated via any suitable method.

Figure 3:
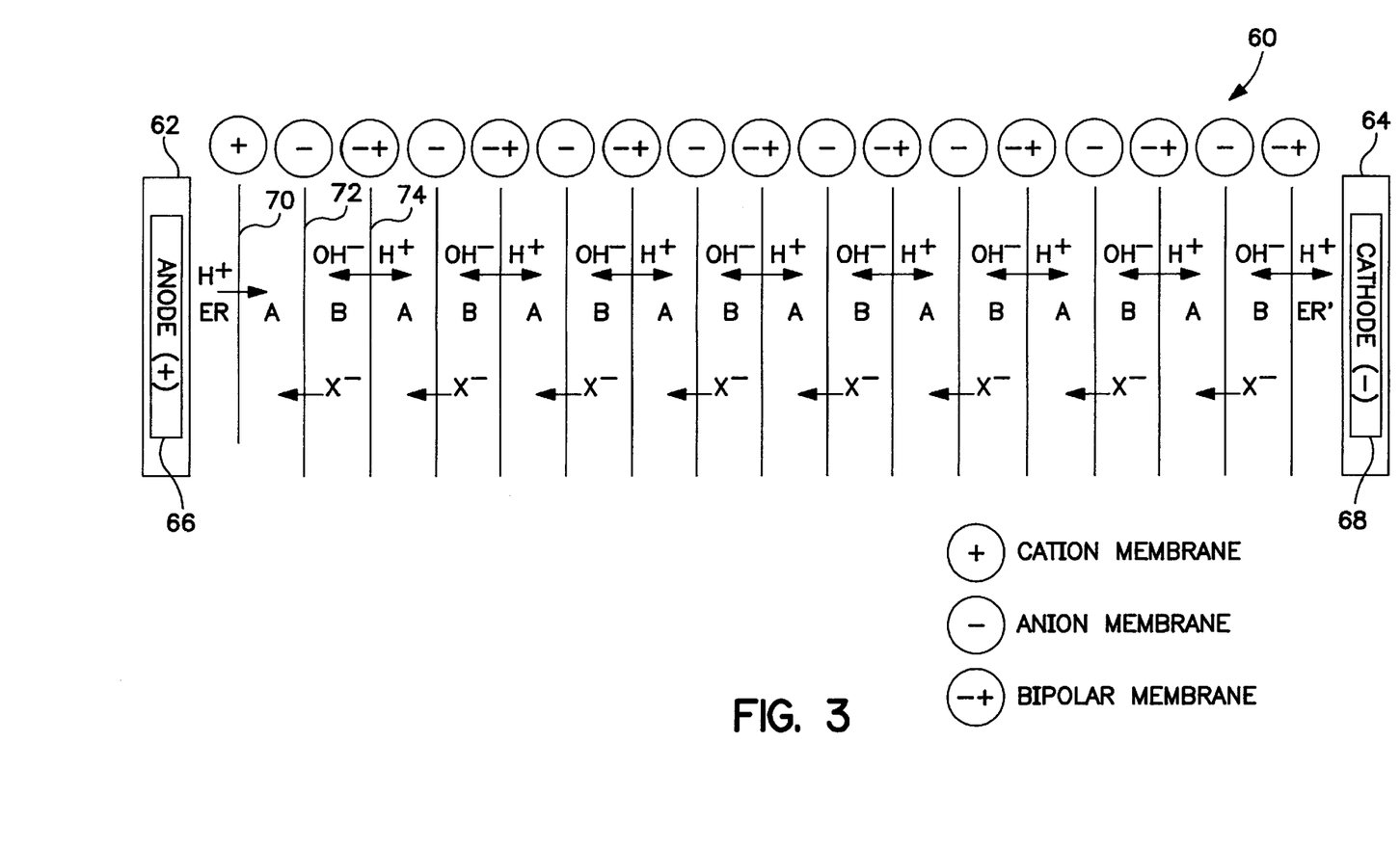
FIG. 3 is a schematic showing of a pilot test cell assembly having a plurality or stack of electrodialysis cells.

A pilot scale electrodialysis stack 60 may be assembled as shown in FIG. 3. The stack has end plates 62 and 64 with electrodes 66, 68 attached thereto. Solutions were fed into and removed from the stack via electrodes 66, 68. Gaskets 0.76 mm thick are used to separate the membranes and to form the solution compartments A and B. Each gasket had an open central area of 465 cm$^2$ (0.5 ft$^2$), through which a direct current could pass. The open areas are filled with an open meshed screen to keep the membranes separated and to promote good flow turbulence. Holes punched in the gaskets form internal manifolds. Slots (ports) connecting the manifold with the open central area enable parallel flows of the solution into and out of each compartment. The stack has a coated metal (ruthenium) oxide anode 66, supplied by Electrode Products Inc., and electrode rinse compartment (ER), an MC 3475 cation membrane 20 from Sybron Chemicals, and a suitable number of repeating cells, each having an acid compartment A, an AMV or AMT anion membrane 72 from Asahi Glass Company, a base compartment B, and a bipolar membrane 74 from Aqualytics, a division of Graver Water. The last bipolar membrane 74 in the stack is followed by an acid compartment A, an anion membrane 72 (AMV or AMT) a base compartment B, another bipolar membrane 74, an electrode rinse compartment (ER') and a stainless steel cathode 68.

Figure 4:
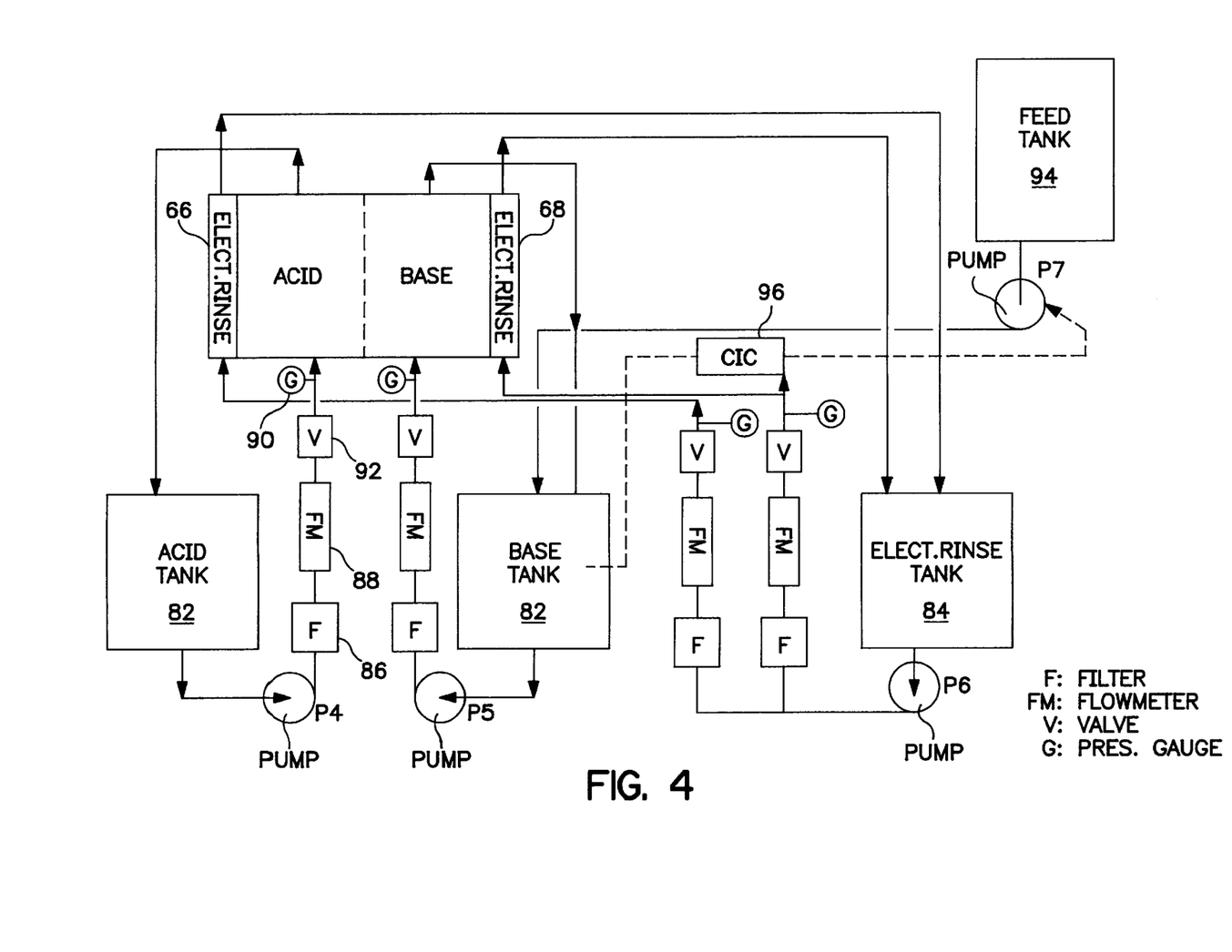
FIG. 4 is a flow chart schematically showing an electrodialysis system.

The stack is placed in the system as shown schematically in FIG. 4, in order to carry out the electrodialysis process. Three pumps (P4–P6) are used to recirculate solutions from their respective tanks to the acid, base and electrode rinse compartments, at a rate of 2–3.5 l/min. Each of the recycle tanks 80,82, 84 has a nominal value of 5 liters. Cartridge filters, such as 86, flowmeters, such as 88, and pressure gauges such as 90, are used to ensure flow of clear fluids at known flow rates and pressure drops in the loops. A suitable valve such as 92 controls the individual stream. A feed pump (P7) is used to supply the filtrate to the base recycle tank 94 under the control of a conductivity controller "CIC" (96)". A DC power supply (not shown) is connected to the anode 66 and cathode 68 terminals of the stack. The requisite controllers for current input and voltage are located at the power supply.

The system is initially charged with the filtrate (feed stream) in both the base 82 and acid 80 recycle tanks. The electrode rinse recycle tank 84 is charged with ~8 wt % sulfuric acid. The recirculating pumps (P4–P6) are started and the flows adjusted at valves such as 92 in order to get an inlet pressure drop of 4–7 psi in each of the loops. The DC current is turned on and the amperage adjusted to obtain an overall voltage of 40 volts or less during the long term tests.

Under the driving force of the direct current, the ammonium salt is converted into ammonium hydroxide in the base loop, while the organic anion that is transported in the acid loop combines with the $H^+$ ion generated at the bipolar membranes in order to yield a free organic acid HX. In the base loop, a salt solution feed stream is added under a conductivity control and the product base is overflowed. In the acid loop, an electro-osmotic transport of water dilutes the product acid concentration to the 2.5–4N range (220–360 gm/l for lactic acid).

EXAMPLE 1

A long term test was carried out in the pilot test cell assembly 60 (FIG. 3) by using a feed material that had been filtered through an ultrafilter, nominally rated at 200,000 Daltons. The eight cell unit 60 had bipolar membranes and AMV anion membranes. The test was operated at a current input of 14.5 A (29 A/ft$^2$ current density). A feed stream with a conductivity of 25 mS/cm was metered into the base recycle tank 82 (FIG. 4) at a rate required to maintain the tank conductivity at ~10 mS/cm. The tank 82 base product at a pH of 9.5–10 was overflowed to waste. The acid product was overflowed from the acid recycle tank 80 under a level control. The base and acid products were somewhat yellow, while the base product was also slightly cloudy. An analysis of the various streams is set forth in Table 3 as follows:

TABLE 3

|  | Dextrose gm/l | Lactic gm/l | Glycerol gm/l | Fumaric gm/l |
| --- | --- | --- | --- | --- |
| Feed | 4.4 | 50.2 | 7.2 | 0.07 |
| Acid Product | 0.6 | 264.5 | 2.68 | 0.17 |
| Base Product | 5.8 | 15.2 | 7.57 | — |

The base product had free ammonia, corresponding to the ammonium in the feed stream, less the amount of the free ammonia that diffused into the acid product. The acid product contained ~0.55 gm/l ammonium ion. The conversion of the organic salt in the base loop was >70%. The retention of dextrose and glycerol in the feed/base stream was 98% and 95% respectively.

Figure 5:
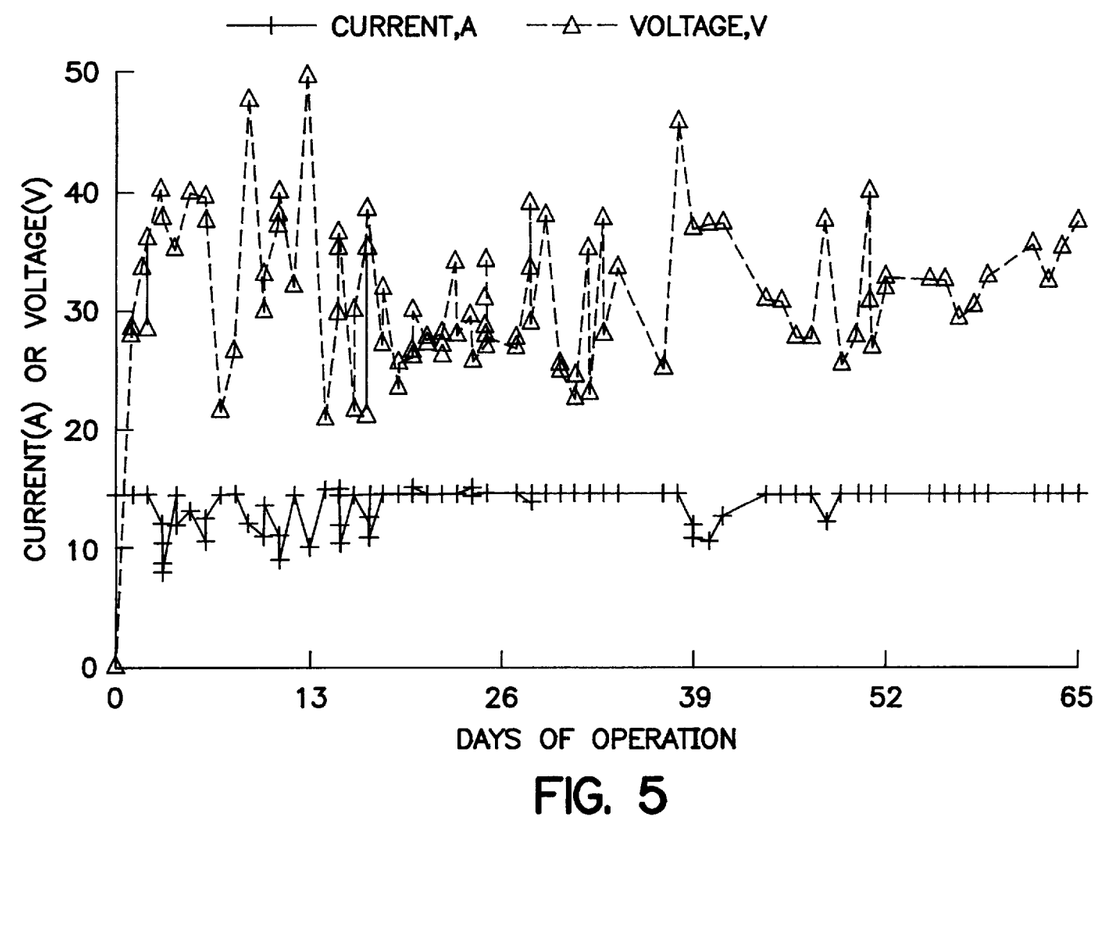
FIG. 5 is a chart showing ultrafiltered feed—AMV anions from eight electrodialysis cells.

FIG. 5 shows the current and voltage profile for the cell stack of FIG. 3 during an extended run which continued for sixty-five days. It can be seen that the voltage drop varied over a large range between 23 and 50 volts. After allowing a 6 volt contribution for the electrode rinse loops, this voltage range translates to 2.12–5.5 volts per cell (one A–B combination in FIG. 3). Operating the process at such high voltages and low current density is expensive and not desirable.

EXAMPLE 2

Another extended term test (FIG. 6) was carried out using the bipolar membranes in conjunction with the AMV anion membranes. The salt feed stream was processed through a Desal 5DK nanofilter, prior to the feed reaching the base loop of the electrodialysis cell. At a typical conductivity of ~25 mS/cm, the feed stream was depleted to 9 mS/cm under a conductivity control, while the organic acid product overflowed from the acid recycle tank 80 (FIG. 4). The feed stream had low levels of divalent metals (Ca+Mg of ~5 ppm) and was essentially free of color. The base tank 82 overflow was clear and had no color in it while the acid product was clear, but with a slightly yellow color indicating that the few remaining color bodies in the feed stream were being transported in their entirety to the acid product. An analysis of the various streams is shown in the following Table 4:

TABLE 4

|  | Dextrose gm/l | Succinic gm/l | Lactic gm/l | Glycerol gm/l | Fumaric gm/l | Acetic gm/l | Ethanol gm/l |
| --- | --- | --- | --- | --- | --- | --- | --- |
| Feed | 1.33 | — | 35.5 | 9.9 | 0.77 | — | 4.68 |
| Acid Product | 0.51 | 4.33 | 295.7 | 4.87 | 9.78 | 2.50 | 1.28 |
| Base Product | 1.33 | — | 8.19 | 10.61 | — | — | 4.97 |

The amounts of succinic and acetic acids in the feed stream were finite but low. Their amounts, as well as the fumaric acid in the base product were near zero because they had been substantially completely transported to the acid loop. Once again the uncharged species such as dextrose, glycerol and ethanol are retained substantially completely (~95% and 98% respectively) in the base loop. Hence, they may be recycled into the fermenter along with the generated ammonia and the unconverted organic salt. The material balance showed that about 80% of the lactate acid and substantially all of the other organic salts had been converted to their free acid form while in the acid loop.

Figure 6:
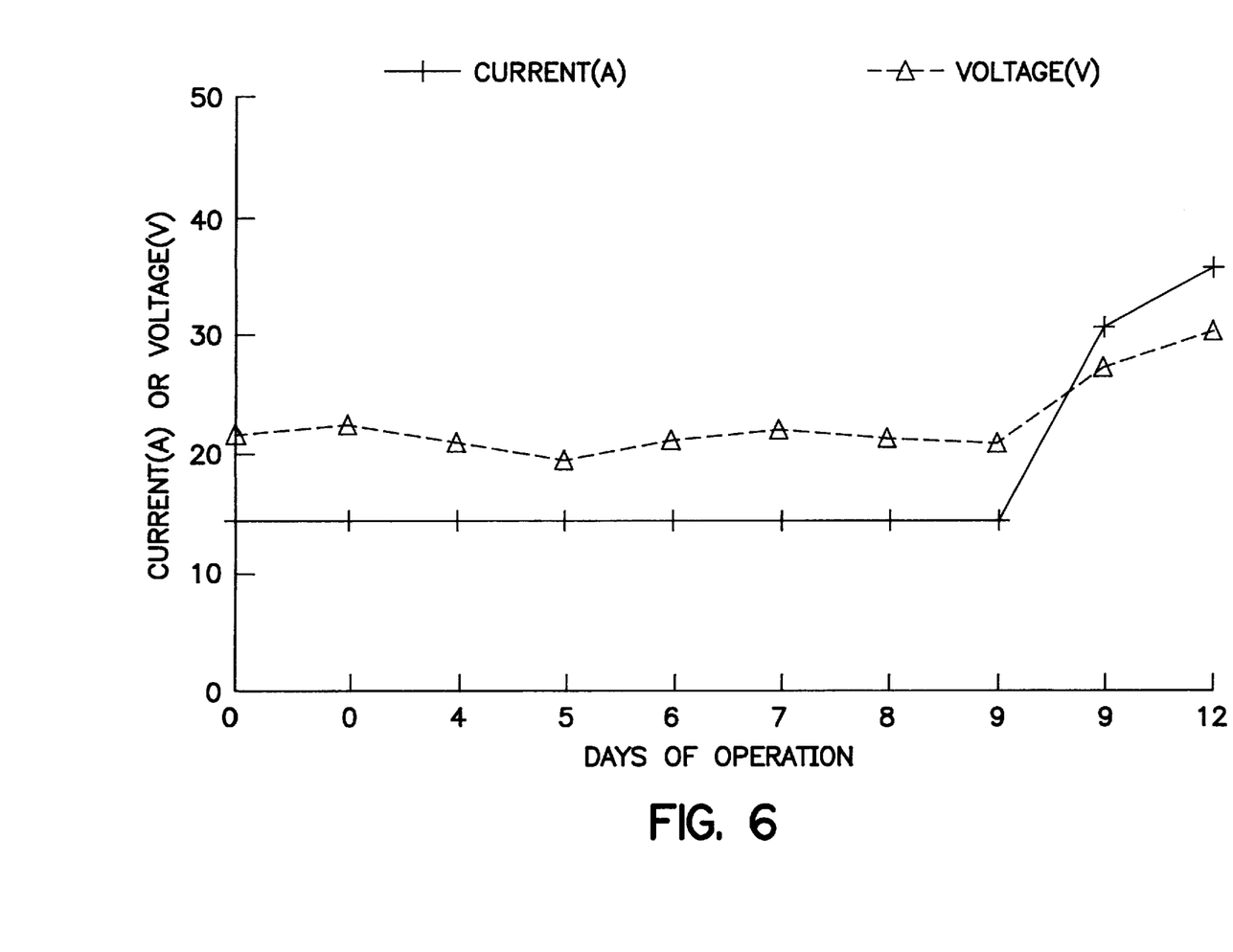
FIG. 6 is a chart showing a nanofiltered feed—AMT anions.

FIG. 6 shows the electrical performance of the electrodialysis cell using the nanofiltered feed. Initially the cell was operated at a current of 14.5 A (29 A/ft$^2$ current density). The voltage requirement remained steady at ~21–22 V (1.87–2.0 V/cell after allowing 6 volts for the electrode rinse loop). Subsequently, the current input was increased to 35 A (70 A/ft$^2$ current density), with a voltage drop of ~31 V (3.1 V/cell). A comparison of these results with the results of Example 1 shows a significant improvement in performance when the nanofiltration is used.

EXAMPLE 3

The sensitivity of the electrodialysis operation to the presence of divalent metals in the feed stream was studied (FIG. 7) in an extended term test by using a cell containing bipolar membranes and AMT anion membranes. A nanofiltered feed stream was used once again. Occasional upsets resulted in higher than desired levels of calcium and magnesium in the feed stream. The cell operating procedures and the compositions of the feed stream acid product, and base product were essentially identical to those in Example 2.

Figure 7:
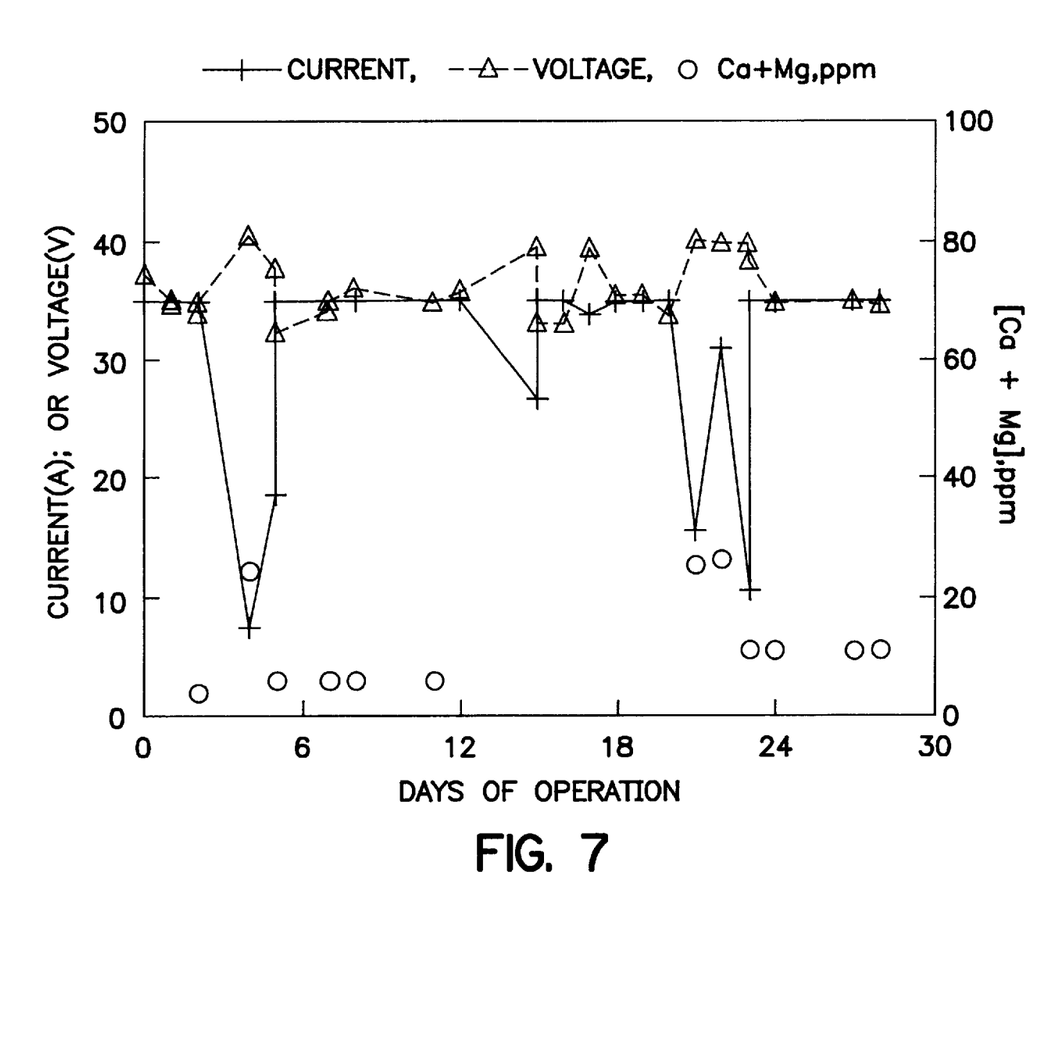
FIG. 7 is a chart showing a nanofiltered—AMT anions.

FIG. 7 shows the performance of the cell during the thirty day test. The cell operated at a current input of 35 A (70 A/ft$^2$ current density) and a voltage drop of 35 V (3.6 V/cell). The higher unit cell voltage is attributable to the higher electrical resistance of the AMT (versus AMV) membrane. However, when the combined concentration of calcium and magnesium exceeded ~10 ppm, the current decreased drastically and the voltage requirement increased. When the divalent metal concentration was brought back to the –10 ppm level and the base loop cleaned out with a dilute hydrochloric acid wash (~5 wt % strength), the cell performance returned to the normal level.

It is clear from the above examples that the operation of the electrodialysis unit is significantly improved by a use of a nanofiltration step. Furthermore, the more complete recovery of the dextrose substrate, the divalent metals, the ammonia base, and the byproducts such as glycerol and ethanol for recycle to the fermenter assures that only the organic acid product of the fermentation process is pulled out of the production loop. A continuous organic acid production process thereby becomes feasible and economical.

Those who are skilled in the art will readily perceive how to modify the invention. Therefore, the appended claims are to be construed to cover all equivalent structures which fall within the true scope and spirit of the invention.

The invention claimed is:

1. A process for recovering organic acids from their ammonium salts, said process comprising the steps of:
    (a) providing a clarified incoming feed stream of an organic ammonium salt solution containing multivalent metal contaminants;
    (b) providing said feed stream of organic ammonium salt solution provided in step (a) by a process of nanofiltration to reduce divalent metal contaminants in said solutions, said metal contaminants being reduced by said nanofiltration to a level below their solubility in an ammonium salt solution;
    (c) passing the ammonium salt solution outflow of step (b) directly into a multi-compartment electrodialysis unit comprising bipolar and anion exchange membranes, and
    (d) applying a direct current driving force across said electrodialysis unit to obtain a concentrated organic acid product and a depleted salt stream containing dissolved ammonia.

2. A process for recovering organic acids from their ammonium salts, said process comprising the steps of:
    (a) providing a clarified incoming feed stream of an ammonium salt solution containing metallic contaminants;
    (b) treating said feed stream of an organic ammonium salt solution by passing said solution through a chelating resin ion-exchange bed in order to reduce divalent metal contaminants in said ammonium salt solutions feed stream, said metal contamination reduction being reduced by said ion-exchange bed to a level below their solubility in the ammoniacal salt solution;
    (c) passing the ammonium salt solution feed stream outflow of step (b) directly into a multi-compartment electrodialysis unit comprising bipolar and anion exchange membranes, and
    (d) applying a direct current driving force across said electrodialysis unit to obtain a concentrated organic acid product and a depleted salt stream containing dissolved ammonia.

3. A continuous process for recovering organic acids and ammonia from their salts, said process comprising, in sequence, the steps of:
    (a) fermenting an incoming saccharide feed stream by a use of microbial cells;
    (b) recovering a feed stream from step (a) by filtering out said microbial cells; and
    (c) treating a feed stream recovered directly from step (b) by a means for removing divalent and multivalent metals selected from a class consisting of a chelating resin ion-exchange bed and a nanofilter for removing said divalent and multivalent metal contaminants therefrom, said metal contaminants being reduced in this step (c) to a level below their solubility in an ammoniac salt solution; and
    (d) processing the feed stream of steps (c) directly through at least two compartments of an electrodialysis unit containing bipolar and anion membranes thereby generating the organic acid and ammonia.

4. The process of any one of the claims 1–3 wherein said removal of said multivalent metal and organic contaminants is via a nanofilter having about a 200 Dalton rating.

5. The process of any one of the claims 1–3 wherein said step of treating said feed stream results in a removal of said metal contaminants to a level which reduces divalent metals ions in said feed stream to a population of less than fifteen parts per million.

6. The process of any one of the claims 1–3 wherein the incoming feed stream is produced by a fermentation step carried out at a pH in the range of approximately 3–9.

7. The process of claim 6 wherein the pH is controlled by a use of a material taken from a group consisting of ammonia and ammonium hydroxide.

8. The process of any one of the claims 1–3 and the further steps of extracting organic acid from an outflow with said metal contaminants removed, and combining the resulting solution with a retentate from said treating step and recycling the combined solution and retentate to an initial step which produces said incoming feed stream.

9. The process of claim 8 and the added step of sterilizing the combination of solution and retentate before recycling it to fermentation.

10. The process of any one of the claims 1–3 wherein said electrodialysis unit is a stack of electrodialysis cells, each cell in said stack having bipolar and anion exchange membranes.

11. The process of either one of the claims 1 and 2, and the further steps preliminary to step (a), said further steps comprising:
    (i) fermenting a saccride feed stream by a use of microbial cells;
    (ii) recovering a feed stream from step (i) by filtering out said microbial cells; and
    (iii) applying the output feed stream of step (ii) as the input feed stream of step (a).

* * * * *